United States Patent [19]

Mortara

[11] 4,090,505
[45] May 23, 1978

[54] ELECTROCARDIOGRAPHIC RECORDING METHOD AND MEANS

[75] Inventor: David W. Mortara, Milwaukee, Wis.

[73] Assignee: Marquette Electronics, Inc., Milwaukee, Wis.

[21] Appl. No.: 691,536

[22] Filed: Jun. 1, 1976

[51] Int. Cl.$^2$ ............................................... A61B 5/04
[52] U.S. Cl. ............................ 128/2.06 G; 346/33 ME
[58] Field of Search ..................... 128/2.06 A, 2.06 B, 128/2.06 G, 2.05 Q; 346/33 ME

[56] References Cited

U.S. PATENT DOCUMENTS

| | | | |
|---|---|---|---|
| 3,552,386 | 1/1971 | Horth | 128/2.06 A |
| 3,616,790 | 11/1971 | Harris | 128/2.06 A |
| 3,654,916 | 4/1972 | Neilson | 128/2.06 A |
| 3,759,248 | 9/1973 | Valiquette | 128/2.06 A |
| 3,824,990 | 7/1974 | Baule | 128/2.06 G |
| 3,878,833 | 4/1975 | Arneson et al. | 128/2.06 A |

FOREIGN PATENT DOCUMENTS

1,202,869  8/1970  United Kingdom ........... 128/2.06 A

*Primary Examiner*—William E. Kamm
*Attorney, Agent, or Firm*—Andrus, Sceales, Starke & Sawall

[57] ABSTRACT

A method and means for graphically recording electrocardiographic data reduces the amount of redundant data displayed so as to reduce the size of the electrocardiogram. However, arrhythmias and other aberrant ekg signal complexes are reproduced in context for diagnostic purposes. Typical or normal signal complexes received from the patient are used to establish an ekg signal complex pattern. In the absence of aberrant signal complexes, this pattern is recorded in lieu of the patient data at a speed which is less than the normal recording speed to form the electrocardiogram. One such pattern may be recorded for every 25 complexes in the patient data, thereby achieving the reduction in the size of electrocardiogram. When an aberrant signal complex occurs, it is entered in the electrocardiogram at the normal higher recording speed. For repetitiously occurring aberrant signal complexes, only certain occurrences of such aberrancies are entered in the electrocardiogram. The proportionality of aberrant to normal signal complexes appearing in the electrocardiogram is thus maintained the same as that appearing in the electrocardiographic data from the patient.

61 Claims, 13 Drawing Figures

ELECTROCARDIOGRAPHIC RECORDING METHOD AND MEANS

BACKGROUND OF THE INVENTION

1. Field of the Invention

The present invention relates to a method and means for graphically recording electrocardiographic data which reduces the amount of redundant data recorded while properly recording atypical events.

2. Description of the Prior Art

The electrical phenomena produced by the physiological functioning of the heart are commonly used for diagnostic purposes. To this end, electrodes are applied at various locations on the body. Leads, connected to the electrodes, are coupled to a galvanometer which detects the difference in electrical potential at the various locations. Typically, the galvanometer drives a pen which displays the potential differences on a moving paper tape in the form of corresponding graphic deflections. The electrocardiogram so produced is visually inspected and analyzed by the cardiologist to obtain the diagnosis. Medically significant features of the electrocardiogram include the duration, magnitude and shape of the voltage deflections. The electrocardiogram is usually retained for reference and comparison purposes. Analysis and storage by a computer is also used.

An electrocardiogram includes a series of voltage deflections for each beat of the heart. A typical or normal heart beat or pulse rate is approximately 70 beats per minute or one beat every 0.8-0.9 seconds (800-900 milliseconds). The cyclical functioning of the heart typically produces a signal complex containing 0.5 seconds of activity which produce potential differences followed by 0.3 seconds of resting in which little or no potential differences are produced.

Since the size, shape and duration of the voltage deflections are extremely important, any workable scheme of electrocardiography must present the electrocardiographic data in a standardized graphic form. This permits comparison of electrocardiograms taken at different times or under different conditions, analysis by different physicians and many other advantages. The format of the paper tape and the recording speed have, therefore, become standardized. The paper tape comprises an elongated chart formed of a plurality of squares. The longer dimension of the chart is used to display time relationships and contains major indicia denoting 0.2 seconds time intervals. The smaller dimension of the grid is used to display voltage magnitudes with major indicia denoting 0.5 millivolt and minor indicia 0.1 millivolt. This chart is run past the galvanometer driven pen at a speed of 25 millimeters per second. To be medically acceptable, any graphic display of electrocardiographic data must correspond to the foregoing format.

There are numerous circumstances in which electrocardiographic data must be recorded over an extended period of time. For example, it may be necessary to compare electrocardiographic data generated by the patient at rest with that generated by the patient under exercise conditions. A standard test of this type including the initial period of normal activity to establish normal electrocardiographic data, the exercise period, and the rest period subsequent to the exercise period, may occupy 10 to 30 minutes. A continuous record of a 10 minute exercise test recorded at the standard speed of 25 mm/sec will produce a paper chart approximately 50 feet long. A 30 minute exercise test would provide an electrocardiogram three times as long.

In intensive cardiac care units, it is necessary to establish even longer term monitoring to include continuous monitoring of all electrocardiographic data for periods of several days.

It will be readily appreciated that the volume of the graphic record produced under these conditions may approach the overwhelming. It becomes impractical for the cardiologist to review this mass of record in detail. As a result, significant, but randomly and/or infrequently occurring unusual phenomena may not be observed. Typical of these phenomena are variations in the rhythms of the heart termed "arrhythmias" which are detected by observing the resulting atypical or aberrant voltage deflections and/or timing in the electrocardiogram.

Heretofore, little opportunity has existed to reduce the size of the recording. While sampling techniques may be employed, there is always the risk that data of medical significance will not be in the sample. Reducing the speed of the chart from the 25 mm/sec standard speed would so change the magnitude and durational relationships of the data with respect to the standardized form as to render such an electrocardiogram useless. Certain features of the electrocardiographic signal might also be lost at reduced recording speed.

SUMMARY OF THE PRESENT INVENTION

The method and means of the present invention provides an electrocardiogram which is reduced in size but in the standard format. The electrocardiogram so provided both contains atypical data received from the patient and displays such data in the proper context with respect to the normal data. As a result, the electrocardiogram is medically acceptable and of greatly enhanced analytical and diagnostic usefulness.

The size reduction obtained by the present invention may hereinafter be termed a "compression" of the electrocardiographic data or chart. While such a compression may be undertaken to varying degrees, a factor approaching 25:1 is typical. Thus, with the present invention, a ten minute exercise test would result in a chart approximately 2 to 3 feet long rather than 50 feet long.

To obtain this compression, normal electrocardiographic signal complexes obtained from the patient are used to form an ekg signal complex pattern which exhibits the characteristics of the normal signal complexes. This pattern may be recorded in the electrocardiogram at reduced speed. For example, instead of the standard speed of 25 mm/sec, a speed of only 1 mm/sec may be employed. The additional electrocardiographic data received from the patient during the slow speed recording continues to be analyzed. Any variations within normal limits are entered in the pattern as an updating. Assuming no aberrant signal complexes are received, the pattern is repetitiously recorded at slow speed to produce the electrocardiogram.

When an aberrant signal complex in excess of normal limits is detected, the recording speed is increased to the normal, fast recording speed and the aberrant signal complex inserted in the electrocardiogram following the completion of the last normal signal complex pattern. Reversion is thereafter made to recording the ekg signal complex pattern at slow speed. When the aberrant phenomena occurs repetitiously, such occurrences are counted and only selected ones of the aberrant signal complex inserted in the electrocardiogram. This maintains the proportionality of the aberrant to normal signal complexes in the electrocardiogram the same as that actually occurring in the electrocardiographic data received from the patient.

Repetitiously occurring aberrancies of different types are separately counted to insure correct insertion and proportionality in the electrocardiogram.

It will be appreciated that only when the data being received from the patient is all normal will a full 25:1 compression be obtained. When aberrant signal complexes appear, the compression ratio is reduced by the amount of fast speed recording required. However, in typical circumstances the overall compression ratio approaches 25:1.

The electrocardiograph of the present invention converts the analog ekg signals from the patient into digital data in an analog-to-digital converter. Signal complexes are identified in the digital data, as in registers, and the complexes so identified applied to a comparator which ascertains whether each complex is normal or aberrant.

Normal signal complexes are provided to an ekg signal pattern register which provides the pattern for slow speed recording. An up-dater is interposed between the comparator and the pattern register so that variations in signal complexes within normal limits may be used to up-date the pattern in the register.

Aberrant signal complexes are provided to an aberrant signal complex register and to a classifier which initially ascertains the types of aberrancies present in the electrocardiographic data. Aberrancy types are stored in storage registers so that the classifier may compare subsequently received aberrancies and classify them by type. The classifier is connected to a counter which records the occurrences of repetitiously appearing aberrant signal complexes. The classifier and counter operate a logic circuit which enters the aberrant signal complex in an aberrant signal complex entry register when such a signal complex is to be inserted in the electrocardiogram.

The ekg signal complex pattern register and the aberrant signal complex entry register are connected to a digital-to-analog converter which operates the pen drive for the electrocardiogram. The pen drive and the drive means for the chart paper may be coordinated from the logic circuit to provide slow speed recording of the ekg signal complex pattern and fast speed recording of the aberrant signal complexes.

BRIEF DESCRIPTION OF THE DRAWING

FIGS. 6C and D show the operation of the electrocardiographic recording means of the present invention under such circumstances in counting the various types of aberrancies appearing in the electrocardiographic data.

DETAILED DESCRIPTION OF THE PREFERRED EMBODIMENT

The Electrocardiographic Signal Complex

Figures 1, 2:
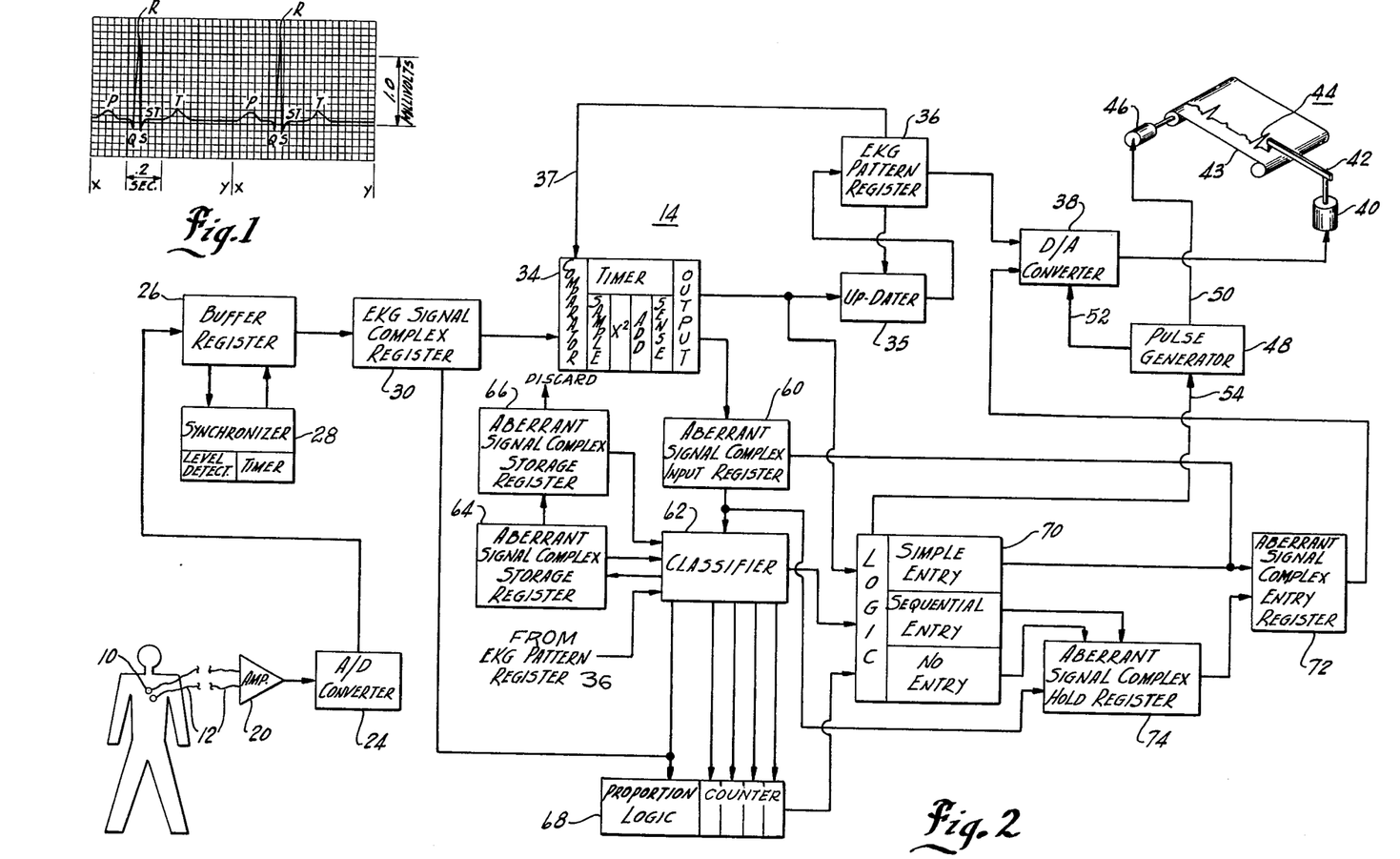
FIG. 1 is a portion of an electrocardiogram showing the format of the moving paper tape and the electrocardiographic signal complexes found in typical electrocardiographic data.
FIG. 2 is a schematic block diagram of the electrocardiographic recording means of the present invention.

FIG. 1 shows the electrical phenomena produced during one typical heart beat. This data is recorded on the moving paper tape or chart described in detail supra, having a grid of squares. The electrocardiographic recording is somewhat diagrammatically shown in FIG. 1, noise and other transient phenomena being omitted.

The initial deflection of the electrocardiographic (ekg) signal complex, the "P wave", is a voltage deflection above the base line produced by the activity of the atria of the heart. The major upward deflection, the "R wave", which is preceded and succeeded by small deflections, Q and S, below the base line, is produced by the ventricles of the heart. The ST segment is an interval following maximum activation of the heart muscle. As the heart muscle relaxes, another voltage difference is produced and is represented by a small upward voltage deflection identified as the "T wave".

One such ekg signal complex is produced for each beat of the heart.

The ekg signals are obtained by a plurality of electrodes placed on the skin of the patient, such as leads 10 shown in FIG. 2. The electrodes are connected by leads 12 to electrocardiograph 14. In conventional electrocardiography, the electrical potential differences between various combinations of leads are simultaneously ascertained and recorded by an electrocardiograph, typically having three recording channels.

Establishing the Ekg Signal Complex Pattern

The present invention provides for the compression of electrocardiographic data by establishing a pattern for the electrocardiographic signal complexes received from the patient which is deemed typical or "normal" for the patient. The typical pattern so established is then recorded on the chart at a speed which is reduced with respect to the normal speed of 25 mm/sec. The speed reduction depends on the amount of data compression desired. For, a theoretical data compression of 25:1 the chart speed would be 1 mm/sec. The reduced recording speed produces an electrocardiographic signal complex on the chart every 20–22 seconds as compared with one electrocardiographic signal complex every 0.8–0.9 seconds in normal recording.

While the slow speed recording is being carried out, additional electrocardiographic data is, of course, being received from the patient at the rate of one signal complex every 0.8–0.9 seconds. Under the example given above, the data from 25 heartbeats will be received while a single electrocardiographic signal complex is being recorded from beginning to end at slow speed. If the subsequently received electrocardiographic data is also normal, there is no need to alter the slow speed recording and the recording of the typical electrocardiographic signal complex continues at the slow speed to produce the electrocardiogram. At the end of one recording of the pattern, the recording is reiterated, commencing at the beginning of the pattern. The pattern is thus repeatedly recorded from beginning to end to produce an electrocardiogram, such as that shown in FIG. 1.

If the subsequently received electrocardiographic data from the patient differs from the ekg signal complex pattern in only minor respects, these differences are used to alter or "up date" the pattern to indicate these changes in the pattern which is recorded at slow speed.

If the subsequently received electrocardiographic data from the patient differs from the ekg signal complex pattern in major, medically significant respects, the complex is identified as aberrant. Atypical or aberrant data is recorded in the electrocardiogram at the normal recording speed.

In FIG. 2 there is shown a schematic diagram of electrocardiograph 14 of the present invention. Electrocardiograph 14 is shown as a plurality of circuitries having the operating characteristics and interconnection shown in the Figure to facilitate an understanding of the invention. It will be appreciate that other circuitries may be employed, including various types of data processing equipment and computers and a Model LSI-11 minicomputer manufactured by the Digital Equipment Corp. of Maynard, Massachusetts has been used in the present invention.

While electrocardiograph 14 may have a plurality of channels, the circuitries for each of these channels are substantially identical and only one such channel is shown in detail in FIG. 2. The circuitry includes an input amplifier 20 which may be of the differential type and include means for establishing a base line for the electrocardiographic data. Such an amplifier may be that shown in U.S. Pat. No. 3,580,243 issued May 25, 1971 and assigned to the same assignee. The output signal of amplifier 20 is an analog signal corresponding to the difference between the electrical potentials in the two leads 12 connected to the input of the amplifier.

This analog signal is converted to a corresponding digital signal in analog-to-digital converter 24 which may for example, sample the analog data 250 times per second and produce a 16 bit word for each sample. The digital signal is recorded in buffer register 26. Buffer register 26 may be a shift register capable of storing a predetermined quantity of electrocardiographic data received from the patient, for example, 750 words or three seconds of data.

Figures 3A, 3B:
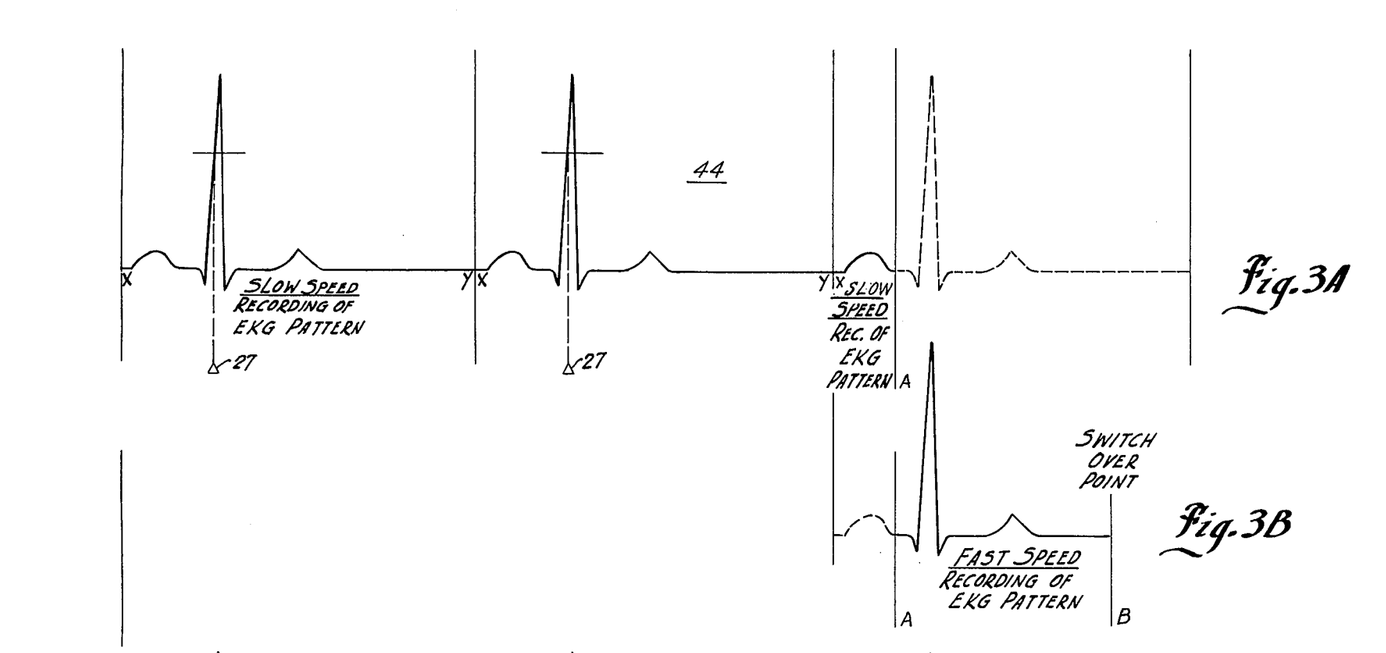
FIGS. 3A through 3C show the insertion of aberrant electrocardiographic data in the electrocardiogram by the present invention.

It is next necessary to identify in the signals from leads 12 and amplifier 20, the data associated with a single heart beat in order to commence establishing the ekg signal complexes. This identification may be done by reference to the major characteristic of the electrocardiographic signal complex, the R wave, produced by ventricular action. A reference point or "marker" in the electrocardiographic signal complex may be established when the "R wave" exceeds the predetermined magnitude. The reference point may be sensed by a level detector in synchronizing circuit 28 and a marker placed at the appropriate address in the data in buffer register 26 so as to identify each heart beat in the data stored in buffer register 26. FIG. 3A shows two such markers 27. In addition to identifying heart beats in the data and as hereinafter noted, the occurrence of markers 27 may be timed to ascertain heart beat intervals, rates, and the like. This may be accomplished by noting the difference in addresses of various markers 27. A rate of change detector may also be used to identify the ekg signal complexes.

The entire ekg signal complex extends from a beginning ahead of the R wave, i.e. ahead of the P wave, to an end subsequent to the R wave, i.e. subsequent to the T wave. The interval between ekg signal complexes is timed in synchronizer 28 as by use of the R wave markers 27 and averaged as for example, over the previous sixteen beats to provide an average interval for the complexes. A starting point or beginning for the signal complex is established by advancing from the reference point 27 by an amount equal to one third of the average beat interval. This establishes the beginning of the ekg complex pattern in advance of the P wave portion. The end of the pattern is established as the beginning time plus the average beat interval. Appropriate addresses may be established in register 26.

There is thus established in the electrocardiographic data in buffer register 26, the portion which is identified as the data associated with one beat of the heart. This portion comprises the "ekg signal complex" and is the data extending from point "x" to point "y" in FIG. 3A.

The ekg signal complex so established by buffer register 26 and synchronizing circuit 28 is then transferred to ekg signal complex register 30 which typically stores the signal complex of one heart beat along with the appropriate address data.

The data in register 30 passes through comparator 34 and up-dater 35 the purpose of which will be hereinafter described, to ekg pattern data register 36.

A readout means 38 which may comprise a digital-to-analog converter is coupled to ekg pattern data register 36 and reads out the electrocardiographic pattern data stored in register 36 to drive motor 40 which energizes pen 42.

the tip of pen 42 is applied to chart 43 which is moved past pen 42 at a speed determined by motor 46. Motor 46 may be a stepper motor, the output speed of which is proportional to the frequency of a pulse train input. The speeds of motor 46 depend on the amount of data compression desired. For data compression of 25:1, a slow speed is provided to motor 46 which moves chart 43 past pen 42 at a speed of 1 mm/sec and a fast speed is provided which moves chart 43 past pen 42 at a speed of 25 mm/sec. The speed of motor 46 is controlled by the output of pulse generator 48 in conductor 50.

The readout of the electrocardiographic pattern data from ekg pattern data register 36 by digital-to-analog converter 38 is correlated to the slow speed of motor 46 by pulse generator 48 by the signal in conductor 52 so that the movements of pen 42 are appropriate for the speed of chart 43. The result is a graphic recording or electrocardiogram 44 produced at a chart speed of 1 mm/sec having the magnitude, shape, and durational relationships which correspond to a conventional electrocardiogram produced at the much higher, conventional speed. It will take approximately 20 to 25 seconds to produce one ekg signal complex in electrocardiogram 44.

FIG. 3A shows the electrocardiogram 44 produced during operation of electrocardiograph 14 in the above described mode. The beginning point "x" and the end point "y" of this data are established by synchronization circuit 28. The configuration of the pattern is established by registers 30 and 36 and comparator 34. Pen 42 traces this data onto the electrocardiogram 44 of chart 43 at the slow recording speed commencing at the beginning point "x" terminating at the end point "y" for the initial pattern, returning to the beginning point "x" and repeating the tracing for a subsequent pattern. The movement of chart 43 places this repetitive pattern in the sequential form.

During the 20–25 second period necessary to produce one ekg signal complex in electrocardiogram 44 at the slow speed, electrocardiograph 14 will continue to receive electrocardiographic data from the patient at the rate of one ekg signal complex every 0.8–0.9 seconds. In the event these subsequently received ekg signal complexes are identical to the ekg pattern data contained in register 36, the electrocardiographic signal complex being recorded on chart 43 is an accurate representation of the condition of the patient's heart so that no alteration in electrocardiogram 44 need be made.

In the event minor variations exist between the subsequently received electrocardiographic data from the patient and the ekg pattern data in register 36, the ekg pattern data is altered to reflect the differences between the data then in the register and that being concurrently received from the patient by electrocardiograph 14.

Comparator 34 is used for this purpose. The incoming electrocardiographic signals from leads 12 are synchronized by synchronizer 28 to identify the ekg signal complexes and provided to ekg signal complex register 30, as described above. From register 30 each complex is applied to comparator 34 in which the new ekg signal complex is compared with the ekg signal complex pattern data already in ekg pattern data register 36. The pattern data may be provided from register 36 by conductor 37. Comparator 34 ascertains whether differences in timing, shape, or magnitude exist between the ekg pattern in register 36 and ekg signal complex provided by register 30 and whether those differences are major or minor. The techniques by which the differences are ascertained and the major or minor significance attached to those differences are described below in connection with the detection of aberrancies.

In the event only minor differences are ascertained between the two signal complexes, the ekg pattern data in register 36 is altered by one-sixteenth of any discrepency between the two signals by means of up-dater 35. Up-dater 35 receives the current pattern from register 36, alters that pattern by one-sixteenth of the differences provided by comparator 34 and reenters the updated pattern in pattern register 36. This technique provides a continuous updating of the ekg pattern data as well as noise reduction through limiting the amount by which the ekg pattern data is altered responsive to changes in the electrocardiographic signals. The updated data is provided by digital-to-analog converter 38 and incorporated in the electrocardiogram 44 recorded on chart 43 as the recording is generated.

Assuming no aberrant electrocardiographic signal complexes are received in leads 12, the above described process continuously repeats itself to provide an electrocardiogram which is compressed by a ratio of 25:1 over conventional electrocardiogram.

Insetions of Aberrant Ekg Signal Complexes

Arrhythmic action of the heart provides an electrocardiographic signal which is unusual or aberrant to a significant degree in timing, magnitude or shape. Such aberrancies are ascertained in comparator 34 by comparing each incoming ekg signal complex with the ekg pattern data in ekg pattern data register 36.

In regard to temporal considerations, a significant alteration in the rate at which the heart is beating is used as a determination of aberrancy. Specifically, if comparison of the incoming ekg signal complex with the ekg pattern indicates that the change of the heart beat rate is more than 25 beats/minute, a determination of aberrancy is made. For purposes of comparison, the interval of the incoming electrocardiographic signal complexes may be determined by ascertaining the location of the address of the marker 27 in the complex undergoing analysis and the address of the marker 27 in the previously received ekg signal complex. The difference in address location is an indication of the interval. This interval is compared with the interval of the electrocardiographic pattern data derived by the averaging process described supra. The intervals are inverted to obtain the heart beat rates. If the difference in intervals is such as to indicate a change of 25 beats/minute or more in the ekg data, a determination of aberrancy is made and the complex entered in aberrant signal complex input register 60. If the change in heart beat rate is less than 25 beats/minute, the interval of the ekg pattern data in the ekg pattern register 36, is altered by one-sixteenth of the interval difference, as described above.

In regard to considerations of shape and magnitude, a mean square deviation analysis is utilized to ascertain aberrancy. For this purpose the amplitude of the ekg signal complex undergoing analysis is taken at a predetermined number of data samplings. The data samplings are typically taken immediately before and after the R wave marker 27 of the electrocardiographic signal complex. Twenty-eight such sampling points may be employed. The data samplings from the incoming ekg signal complex are compared with a corresponding portion of the ekg pattern in register 36. The differences are squared and summed. If the sum of the squares of the signal differences exceeds a predetermined magnitude, a determination of aberrancy is made. If the sum of the squares does not exceed the predetermined magnitude, the ekg pattern data is updated in the manner described above. In this updating, one-sixteenth of the differences are applied to the ekg pattern data. These differences are not squared and all differences, not just those of the sample, are employed.

Aberrant signal complexes detected by comparator 34 are provided to aberrant signal complex input register 60. The details of the circuitry for processing aberrant signal complexes are described infra in connection with "Recording of Different Types of Aberrancies". Such circuitry includes a logic circuit 70 which ascertains when the aberrant signal complex is to be inserted in electrocardiogram 44. If such is the case, the aberrant signal complex is entered in aberrant signal complex entry register 72 connected to digital-to-analog converter 38. Logic circuit 70 is connected to pulse generator 48 by conductor 54 to control the readout rate of digital-to-analog converter 38 and the speed of chart motor 46.

When the occurrence of an aberrant signal complex is to be entered in electrocardiogram 44 logic circuit 70 operates pulse generator 48 to accelerate motor 46 to the normal recording speed of 25 mm/sec. The operation of pen motor 40 is correspondingly accelerated. The recording of the ekg pattern from register 36 is completed at the high speed. At the appropriate point in the electrocardiographic pattern, the aberrant ekg signal complex is inserted in the electrocardiogram 44 so that its presence is recorded and it appears in the proper context.

Figure 3C:
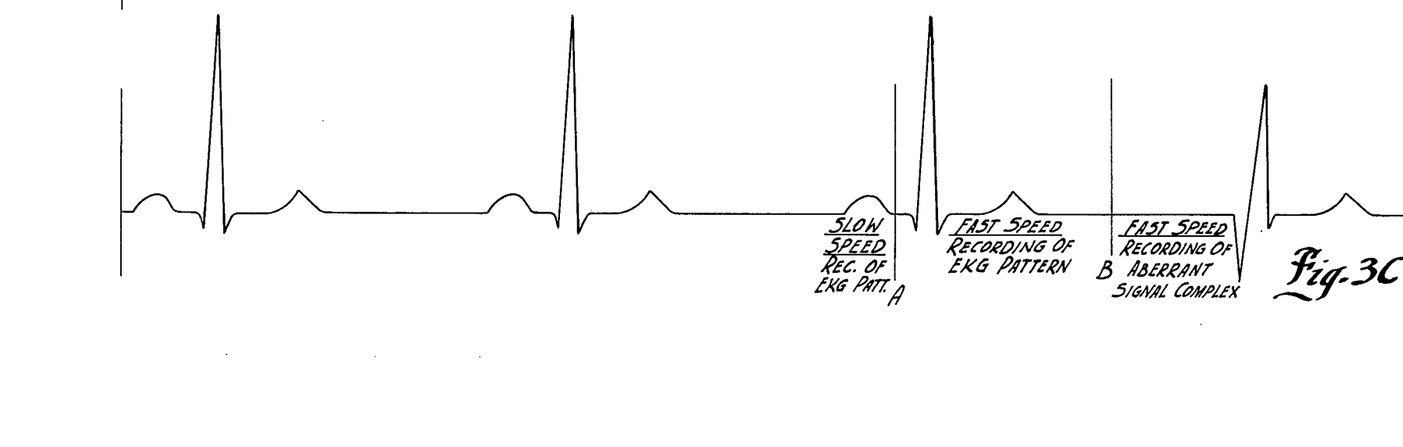
Figure 4A:
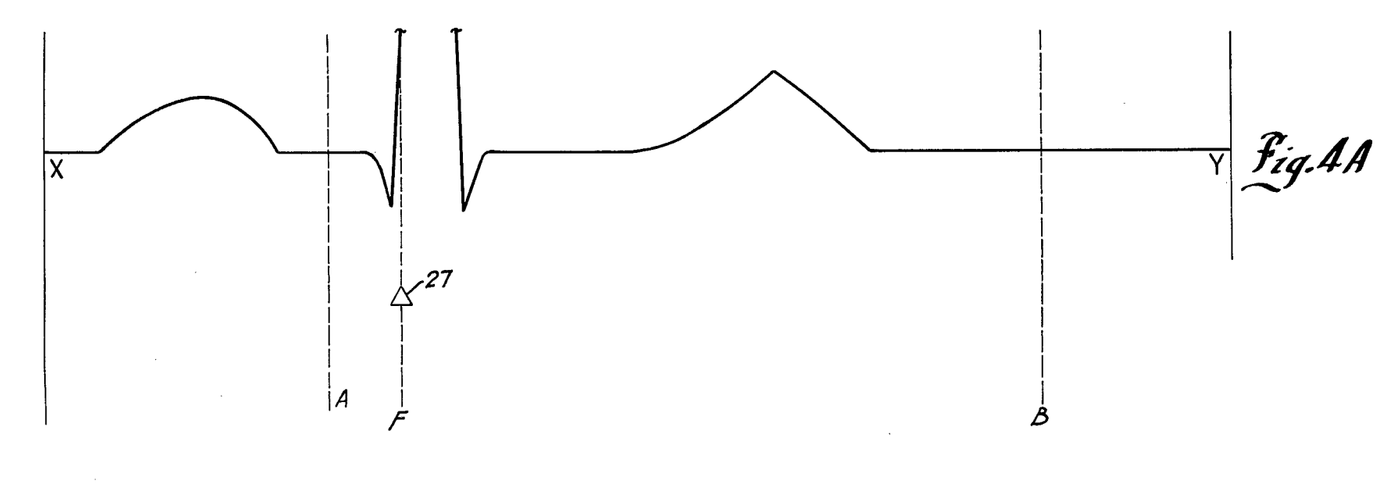
FIG. 4A is an electrocardiogram containing a single electrocardiographic signal complex in a greatly enlarged scale.
Figure 4B:
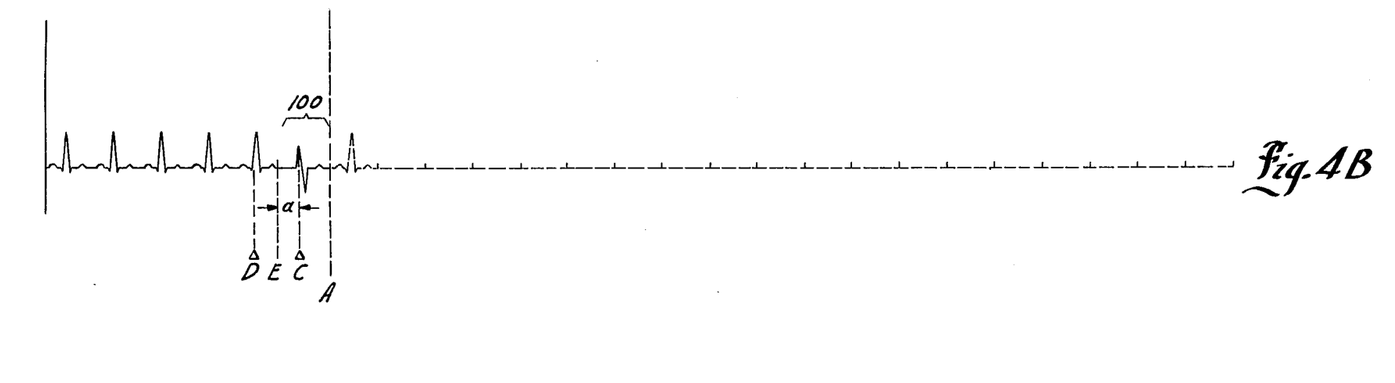
FIG. 4B shows electrocardiographic data received from the patient during the recording of the electrocardiogram shown in FIG. 4A.

The operation of electrocardiograph 14 in the insertion of arrhythmic complexes may be shown by reference to FIGS. 3A–3C and 4A and 4B. The electrocardiogram 44 of FIG. 3A is produced by normal operation of electrocardiograph 14 in which no aberrant data such as arrhythmias are received from the patient. As noted supra, the ekg pattern data from register 36 is repetitiously recorded to provide the electrocardiogram. FIG. 4A shows an enlargement of a single ekg signal complex, the recording of which at the slow speed would ordinarily require 20 seconds. The vertical scale of FIGS. 4A and 4B has been enlarged commensurate with the horizontal scale to maintain perspective. If 20 seconds were required to record the ekg signal complex at the slow speed, the data from 25 heart beats would be received by electrocardiograph 14, several of which are shown in FIG. 4B.

Each of these 25 subsequently received beats are analyzed for aberrancy by comparator 34. Such an aberrancy is shown as the sixth beat 100 in FIG. 4B. The detection of the aberrant beat may occur at point A in FIGS. 3B and 4B. Point A is subsequent to the point identified as "x" in FIGS. 3A and 4A at which the slow speed recording of the ekg signal complex pattern from register 36 has commenced. Assuming the aberrant event is to be entered in electrocardiogram 44, upon detection at point A, logic circuit 70 provides a signal in conductor 54 to pulse generator 48 to accelerate motor 46 and chart 43 to the faster recording speed of 25 mm/sec. The operation of readout means 38 and pen motor 40 is similarly coordinated to maintain the proper configuration to the electrocardiogram. Pen motor 40 continues to be driven by the ekg pattern data in register 36. As a result the ekg pattern data is recorded at fast speed, as shown in FIG. 3B.

This continues until an appropriate switch over point is reached at which the generation of the electrocardiogram from the ekg pattern data is terminated and insertion of the aberrant ekg signal complex into the electrocardiogram is commenced. Such a switch over point may be established at point B shown in FIG. 3B and C and FIG. 4A. At switch over point B, the operation of pen motor 40 from ekg pattern data register 36 is terminated and pen motor 40 is driven from the aberrant ekg data in aberrant signal complex entry register 72 to insert the aberrancy in the electrocardiogram.

In establishing the switch over point from ekg pattern data in register 36 to the aberrant data in register 72, several considerations are important. One is that the insertion correctly reflect the interval between the arrhythmic beat and the previous normal beat. This preserves this medically significant aspects. It is further important to record the concluding portion of the last normal beat. Any preceding phenomena which may have cause the aberrant cardiac signal complex is this fully recorded.

The switch over point may be established in comparator 34 when detection of an aberrant signal complex occurs. The interval between the aberrant signal complex and the last normal signal complex is ascertained, as by reference to the R wave markers 27 in the ekg signal complexes established in buffer register 26. This time period may be the interval C – D shown in FIG. 4B. A predetermined interval "a", for example, 0.2 seconds is subtracted from the C – D time interval to establish point E. The location of this point reflects the interval between the arrhythmic complex and the last normal complex. The point also occurs before the conclusion of the last normal signal complex preceding the aberrant complex.

In the ekg signal complex pattern shown in FIG. 4A, the R wave marker 27 is identified at point F. This marker 27 at point F corresponds to point D in the last normal complex preceding the arrhthymic complex. Point F in the ekg signal complex pattern and point D in the last normal signal complex assume identical reference points. The interval D – E may then be added to the point F of the ekg signal complex pattern to establish the point B which corresponds to point E. The interval F – B in the pattern therefore corresponds to the interval D – E in the incoming ekg data containing the aberrant ekg signal complex 100 so by switching from the ekg pattern to the aberrant signal complex at point B and recording all incoming ekg data subsequent to point E the correct interval will be maintained. Such recording also enters the concluding portions of the last normal beat subsequent to point E into the electrocardiogram. Comparator 34 inserts point B in the data in pattern register 36.

The resulting electrocardiogram 44 is shown in FIG. 3C. Prior to the detection of the aberrant ekg signal complex at point A, the electrocardiogram is formed by slow speed recording of the ekg signal complex pattern. At point A high speed recording of the ekg pattern commences and continues until the switch over point B. When point B is reached the precedence of the recording from pattern register 36 is lost and high speed recording of the aberrant signal complex takes over.

In the event the aberrant ekg signal complex is detected subsequent to the switch over point B, the recording of the ekg pattern from register 36 must be repeated at the high speed recording until the switch over point in the subsequent ekg signal complex pattern is attained. Entry of the aberrant signal complex occurs at that point. Should the point B fall beyond point $y$, i.e. to the right to $y$ when viewed as in FIG. 4A, the base line magnitude existing at point $y$ is recorded until point E in the incoming ekg data from the patient is reached, at which time recording of the aberrant ekg signal complex commences. This extension of the base line retains the continuity in the electrocardiogram.

Assuming the aberrant ekg signal complex 100 is an isolated occurrence, electrocardiograph 14 reverts to recording the pattern in ekg pattern register 36 as soon as the aberrant signal complex has been entered in the electrocardiogram. The fact that the next ekg signal complex received by electrocardiograph 14 subsequent to the aberrant signal complex is normal is ascertained in comparator 34. When the end of the aberrant signal complex is reached, i.e. at point $y$ of the aberrant signal complex, the precedence recording of from the aberrant signal complex entry register is lost and recording of the ekg signal complex pattern from register 36 resumes from point $x$ of the pattern. Logic circuit 70 provides the appropriate signals to digital-to-analog converter 38 and pulse generator 48 to resume the slow speed recording of the pattern.

Recording of Recurrent Aberrant Phenomena

The foregoing describes the technique by which an aberrant ekg signal complex is inserted in electrocardiogram 44 when the appearance of the aberrant signal complex is generally isolated in occurrence.

More commonly, however, aberrancy in the signal complexes is a recurring phenomena. For example, an aberrancy in the functioning of the heart may be followed by a series of normal beats, after which the aberrancy again appears. For example, one aberrant signal complex may be followed by seven normal or typical signal complexes; another aberrant signal complex; seven more normal signal complexes; and so on. The ratio of typical signal complexes (T) to aberrant signal complexes (A) or (T/A) is thus 7:1. If the electrocardiogram 44 produced by compressed recording to be a true indication of the electrocardiographic data received from the patient, it must show the identical 7:1 proportionality between aberrant signal complexes and normal signal complexes.

To produce such an electrocardiogram, electrocardiograph 14 operates to initially record seven ekg signal complex patterns at slow speed, after which one aberrant signal complex is inserted at high speed. Slow speed recording of seven more ekg signal complex patterns is thereafter resumed, again followed by high speed recording of another aberrant signal complex.

In electrocardiograph 14, the slow speed of chart 43 of 1 mm/sec. is 1/25th the fast speed of 25 mm/sec. This means that as a result of the slow speed recording, one ekg signal complex pattern recorded at slow speed is the equivalent of, or equal to, 25 heart beats, both normal and aberrant in the electrocardiographic data received from the patient.

At the end of the seventh slow speed ekg signal complex pattern, it is necessary to select an aberrant signal complex from the electrocardiographic data received from the patient which will be entered in electrocardiogram 44. During the recording of the seven ekg signal complex patterns at slow speed, 175 electrocardiographic signal complexes, both normal and aberrant, will have been received from the patient by electrocardiograph 14. Of these, one-eighth or 21 will be aberrant. This suggests entry of the 21st aberrant signal complex into the electrocardiogram. The foregoing may be more generally expressed as $$A/R \times 25\, T/A \tag{1}$$

where:
- R = the total number of signal complexes in the sample
- T = the number of typical signal complexes in the sample
- A = the number of aberrant signal complexes in the sample
- 25 = the ratio of fast chart speed to slow chart speed However, consideration must be given to the fact that for an aberrant signal complex to be entered in electrocardiogram 44 it must occur prior to the switchover point B shown in FIGS. 3 and 4. Use of the 21st aberrant signal complex in the example given above, may be so late as to cause the inclusion of an eighth pattern before the aberrant complex may be inserted. The foregoing indicates the use of an aberrant signal complex earlier than the 21st one, to insure that the aberrant signal complex will be properly entered in electrocardiogram 44.

Since it is unlikely that the switchover point B will ever be located ahead of the middle of the ekg signal complex pattern, reducing the count by an amount corresponding to one half a pattern will insure proper entry. When expressed in terms of number of aberrant signal complexes, this one half pattern represents ½ × 25 (A/R), the one half and the 25 representing the one half of 25 complexes/pattern, and the A/R representing the occurrence fraction of the aberrant signal complexes. To provide the necessary compensation, the one half pattern is subtracted from formula (1) to ascertain which aberrant signal complex will be entered in the electrocardiogram. Formula (1) becomes Aberrant signal complex to be entered in
$$\text{electrocardiogram } (N) = A/R\, [25\, T/A - \tfrac{1}{2} \cdot 25 \cdot A/R]\text{ or} \tag{2}$$

$$A/R \times 25\, [T/A - \tfrac{1}{2}\, A/R]\text{ or} \tag{3}$$

$$25\, [T/R - \tfrac{1}{2}\, A/R] \tag{4}$$

Applying formula (4) to the example used above of seven normal complexes and one abnormal complex gives 25 (⅞ − ½ · ⅛) = 20.31. Thus, use of the 20th complex as derived from formula (4) rather than use of the 21st complex as derived from formula (1) will insure proper entry of the aberrant signal complex in the electrocardiogram.

Figure 5A:
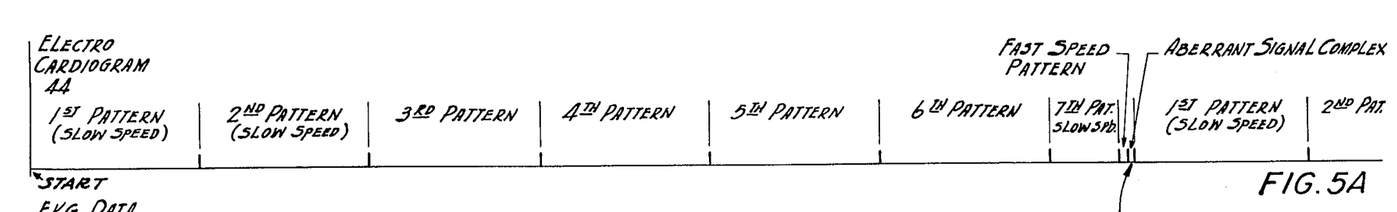
FIG. 5A shows, in a high schematic form, the generation of the electrocardiogram by the present invention.
Figure 5B:
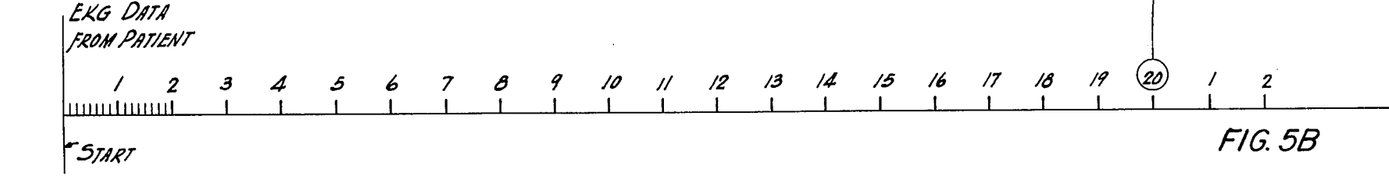
FIG. 5B shows, also in highly diagrammatic form, the electrocardiographic data received from the patient during the generation of the electrocardiogram shown in FIG. 5A under conditions in which a single type of aberrant signal complex is present in the electrocardiographic data from the patient.

The foregoing operation of electrocardiograph 14 may be graphically seen by reference to FIGS. 5A and 5B. FIG. 5A in a highly schematic form shows electrocardiograph 44 containing the ekg signal complex patterns recorded at slow speed and the aberrant signal complexes recorded at fast speed. FIG. 5B similarly shows the electrocardiographic data received from the patient. Each signal complex in the electrocardiographic data from the patient is indicated by a vertical line in FIG. 5B. Thin vertical lines represent typical complexes while the thick vertical lines, identified by numbers, represent aberrant complexes. Thus the first seven heart beats in electrocardiographic data are typical and the eighth beat is aberrant. The next seven beats are typical and the following beat is aberrant. The typical heart beats in the electrocardiographic data are only shown for the first 14 beats.

At the left hand side of the drawing, labelled Start, it may be assumed that an aberrant signal complex has been recorded and electrocardiograph 14 has just returned to slow speed recording of the ekg signal complex pattern from register 36. In order to find the 20th aberrant signal complex it is necessary to count the aberrant signal complexes appearing in the electrocardiographic data from the patient. The increasing total count is shown by the numbers over the aberrant signal complexes in FIG. 5B.

In accordance with formula (4) the 20th aberrant signal complex will be inserted in electrocardiogram 44. It will be noted from FIGS. 5A and 5B that by the time twenty aberrant signal complexes have appeared in the electrocardiographic data from the patient the seventh ekg signal complex pattern is being recorded in electrocardiogram 44.

As the 20th aberrant signal complex is to be inserted in electrocardiogram 44, when it appears in the data the sequence described above under "Insertions of Aberrant Ekg Signal Complexes" occurs. The recording of the seventh ekg signal complex pattern is completed at fast speed and thereafter the 20th aberrant signal complex is inserted into the electrocardiogram. This is shown in FIG. 5A. FIG. 5A shows the combined slow speed-fast speed recording of the seven ekg signal complex patterns and the fast speed recording of the 20th aberrant signal complex.

At the completion of the insertion of the 20th aberrant signal complex, the slow speed recording of the ekg signal complex patterns is recommenced as is the counting the aberrant signal complexes received in the electrocardiographic data from the patient. When 20 aberrant ekg signal complexes have again been received, the above described operation is repeated to insert another aberrant signal complex into electrocardiogram 44.

Selection of the aberrant signal complex to be written in electrocardiogram 44 in accordance with formula (4) is particularly important when the aberrant signal complexes are frequently occurring in the electrocardiographic data for the patient, for example, every other signal complex (digeminy) or every third signal complex (trigeminy). Unless formula (4) is followed, a condition of trigeminy may appear as three normal signal complexes followed by an aberrant signal complex rather than appearing as true trigeminy, i.e. in the ratio of 2:1.

Recording of Different Types of Aberrancies

The foregoing has dealt with the insertion of an aberrant signal complex of only one type. The electrocardiographic data received from the patient may also be aberrant in several respects so that two or more different types of aberrant signal complexes may be encountered. The operation of electrocardiograph 14 under conditions in which a plurality of different aberrant signal complexes is encountered is as follows.

As noted supra, only a fraction of the aberrant signal complexes, for example 1/20th of the aberrancies, are actually inserted in electrocardiogram 44. This will be true of each type of aberrancy which is present in the electrocardiograhic data. Since the fractional whole is equal to the sum of the practional parts, the same fraction of each type of aberrancies making up the whole must be entered in electrocardiogram 44. This recording is achieved by counting each type of aberrancy separately and recording every 1/N occurrence of each type of aberrancy or $1/N\ A_1 + 1/N\ A_2 \ldots 1/N\ A_n$.

For example, assume a situation in which there are three typical signal complexes, a first type of aberrant signal complex ($A_1$) three more typical signal complexes and a second type of aberrant signal complex ($A_2$). FIG. 6B is a schematic representation of this electrocardiographic data in a format similar to that of FIG. 5B. The typical complexes are shown by thin lines and the aberrant signal complexes are shown by thick lines identified by the type of aberrancy, $A_1$ or $A_2$, which they represent. For a complete data sample the number of aberrant signal complexes is two, i.e. one $A_1$ and one $A_2$. The number of typical complexes is six and that total is eight.

Formula (4) when incorporating the above quantities provides $$26\ (6/8 - \tfrac{1}{2} \cdot 2/8) = 15.63$$

Figure 6A:
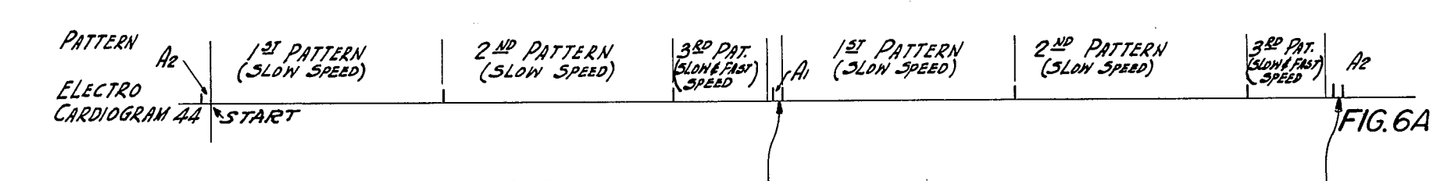
FIGS. 6A, B, C and D are similar to FIGS. 5A and B and show, in highly schematic form, the generation of an electrocardiogram and the electrocardiographic data received from the patient when two types of repetitiously occurring aberrant signal complexes are present in the data.
Figure 6B:
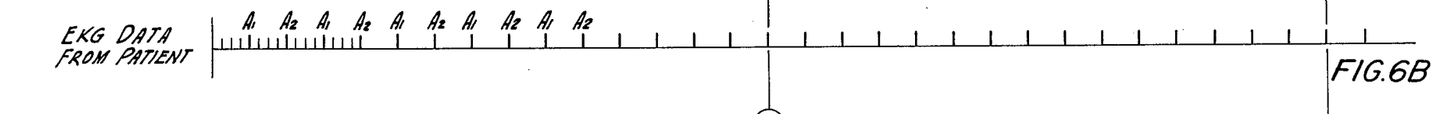

Thus, every 15th ekg signal complex will be entered in the electrocardiogram 44 shown in FIG. 6A.

Figure 6C:
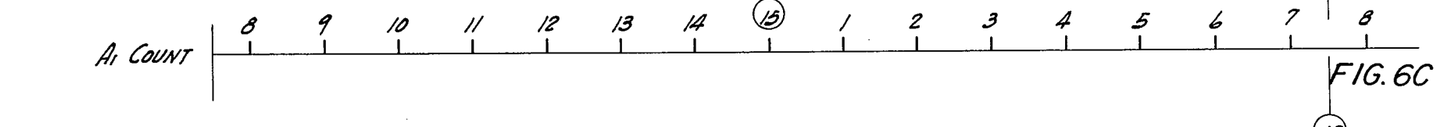

Assume a starting condition in which an $A_2$ aberrant signal complex has been entered in the electrocardiogram 44 and slow speed recording of the ekg signal complex pattern has just resumed. At the starting point it may be assumed approximately seven $A_1$ aberrant signal complexes have been received by electrocardiograph 14 as indicated in FIG. 6C which shows the count of $A_1$ aberrant signal complexes received. The counting of the $A_1$ aberrant signal complexes continues during the slow speed recording of the ekg signal complex patterns from register 36. The receipt of the 15th aberrant $A_1$ signal complex will occur approximately half way through the third pattern recording. As the 15th aberrant signal complex is to be inserted in electrocardiogram 44, when it appears, the third pattern is completed at the fast speed and the $A_1$ aberrant signal complex entered as shown in FIG. 6A - C.

Figure 6D:
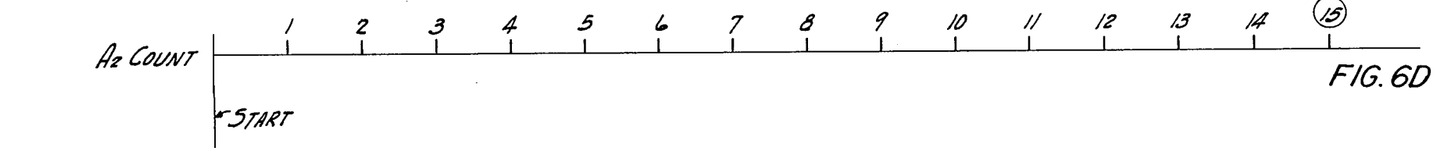

Slow speed recording of the ekg signal complex pattern from register 36 is then resumed. The counting of the $A_1$ aberrant signal complex resumes again from 1. The counting of the $A_2$ aberrant signal complexes continues, as shown in FIG. 6D.

By the time 15 $A_2$ aberrant signal complexes have been received, electrocardiograph 14 will have recorded two more full ekg patterns at slow speed and will be engaged in the writing of the third pattern. When 15 $A_2$ aberrant signal complexes are received in the electrocardiographic data from the patient, electrocardiograph 14 operates to complete the third pattern at high speed. Thereafter, the $A_2$ aberrant signal complex is entered in electrocardiogram 44, as shown in FIGS. 6A, B, and D.

Should the starting counts in the counters be different than that shown in FIGS. 6C and D the place of insertion of the aberrant signal complexes in electrocardiogram 44 will vary from that shown. However, the proportion of typical to aberrant signal complexes will be in accordance with the ekg data from the patient.

Returning now to the circuitry of FIG. 2, when an ekg signal complex from register 30 is determined to be aberrant by comparator 34, it is provided to aberrant signal complex input register 60. The aberrant signal complex in register 60 is applied to classifier 62 which ascertains the nature of the aberrancy and classifies the signal complex accordingly. While aberrant signal complexes may be analyzed for a number of aberrant characteristics, a typical embodiment of the present invention may identify two different aberrant shapes ($A_1$ or $A_2$) in the aberrant signal complexes. Additionally, aberrant timing of all signal complexes will be detected. Classification of the aberrant complexes is summarized in accordance with the following tabulation.

| Aberrancy Type | Shape | Timing | |
|---|---|---|---|
| #1 | normal | premature | |
| #2 | normal | late | subject to counting |
| #3 | aberrant in 1st respect ($A_1$) | premature | |
| #4 | aberrant in 2nd respect ($A_2$) | premature | |
| #5 | aberrant in any respect | normal | always entered |
| #6 | aberrant in any | late | |

| Aberrancy Type | Shape | Timing |
|---|---|---|
| | | respect |

The foregoing classification may utilize the analytical techniques for shape and timing described above in connection with comparator 34.

Storage means are provided in connection with classifier 62 to assist in classifying the aberrancies. For types #1 and #2 aberrancies which are normal in shape but atypical in timing, the ekg signal complex pattern in register 36 may be used to classify these aberrancies. The ekg pattern register 36 is shown in duplicate in dotted lines to show its connection with classifier 62. The prematurity or lateness of the timing is also ascertained with respect to the ekg signal complex pattern as by means of the loxation of markers 27 accompanying each of the signal complexes.

For aberrancies having an aberrant shape and premature timing, when the first such aberrant signal complex is received, it is stored in aberrant signal complex storage register 64 to become aberrant signal complex type #3. Subsequent complexes of this type are compared against this stored data on the basis of shape on the sampling basis described in connection with comparator 34. The ekg signal complex pattern is used for comparative purposes in determining timing.

When a premature, aberrant signal complex having a shape which differs from the aberrant signal complex type #3 in storage register 64 is received, the aberrant signal complex type #3 is moved to aberrant signal complex storage register 66 and the differing aberrant signal complex becomes aberrant signal complex type #4 which is then stored in aberrant signal complex storage register 64. The data in both registers 64 and 66 is available for classifying subsequently received aberrant signal complexes. Should additional aberrancies be received which resemble neither of the stored types #3 and #4 aberrant data, the new aberrant signal complex is stored in storage register 64. The aberrant signal complex data already in storage register 64 is moved to storage register 66 and the aberrant signal complex data in aberrant signal complex storage register 66 is discarded. In this manner, the last two aberrant signal complexes are, at all times, stored in storage registers 64 and 66 for use by classifier 62.

Aberrancy types #5 and #6 are relatively rare from a physiological standpoint and are always entered in electrocardiograph 44 whenever they appear.

Aberrancy types #1 through #4 are the more common aberrancies. These types of aberrancies are subject to the counting described above and shown in FIGS. 5 and 6.

Each time an aberrant signal complex is provided to classifier 62, it is compared with the data stored in storage registers 64 and 66 and ekg pattern register 36. If it is found to be of any of the types #1 through #4 a count is then entered in the corresponding counting section of counter 68. Counter 68 may include four sections for counting each of the four different types of aberrancies. The proportion logic portion of counter 68 is connected to ekg signal complex register 30 and to classifier 62 to receive the data necessary to determine the count, or proportion, to be entered in counter 68 and used to determine the aberrant signal complex, such as the 15th or 20th, to be entered in electrocardiogram 44. This count may be obtained by using a data sample comprising the immediately preceding 25 signal complexes applied to electrocardiograph 14. The same count is employed in all sections of counter 68. Counter 68 may be of the count up or count down type.

Classifier 62 and counter 68 are connected to logic circuit 70 which controls the entry of the aberrant signal complexes into electrocardiogram 44. The logic circuitry 70 operates in accordance with the following rules. First, when an aberrant signal complex of types #1 through #6 occurs and when the subsequent signal complex is also a type #1 through #6 aberrant signal complex, both signal complexes are entered in electrocardiogram 44 to show the sequence of two aberrant signal complexes. This instance may be termed "sequential entry". Second, and as noted supra, when types #5 and #6 aberrancies occur, these are always entered in electrocardiogram 44. Third, when a type #1 through #4 aberrancy occurs and the count of such aberrancies has attained that set in counter 68, that aberrant signal complex will be entered in electrocardiogram 44. These last two instances may be termed "simple entries". The first occurrence of a #1 through #4 aberrancy will always be entered in electrocardiogram 44. This may be accomplished by the setting of the counter 68, as by use of a count down counter.

The operation of logic circuit 70 in the case of simple entry is as follows, using the example of FIGS. 5A and B in which only single type of aberrant signal complex is involved. When the 20th aberrant signal complex is provided to classifier 62 and found to be aberrant by comparison to the data in storage register 64, the 20th count is provided to counter 68. Counter 68 provides a signal to logic circuit 70 which causes the circuit to transfer the 20th aberrant signal complex in classifier 62 to aberrant signal complex entry register 72. Logic circuit 70 also operates pulse generator 48, motor 46 and digital-to-analog converter 38 to commence the fast speed recording of the remainder of the ekg signal complex pattern from register 36 and the subsequent entry of the aberrancy signal complex from register 72 in electrocardiogram 44. At the conclusion of this entry, pulse generator 48, motor 46, and digital-to-analog converter 38 are operated to revert to the slow speed recording of the ekg signal complex pattern from register 36. Counter 68 is reset.

In the event a type #5 or #6 aberrant signal complex is detected by classifier 62, logic circuit 70 is operated to place this aberrant signal complex in entry register 72 for entry into electrocardiogram 44.

In the event two aberrant signal complexes apparent in sequence, the operation of logic circuit 70 is as follows. Each time an aberrant signal complex is placed in aberrant signal complex input register 60 it is also placed in aberrant signal complex hold register 74. The data is held there by a blocking "no entry" signal from logic circuit 70. In the event the next signal complex is normal, as indicated by the output of comparator 34, no further use is made of the data in hold register 74 and the data is replaced by the next aberrant signal complex. If, however, the next signal complex is aberrant, logic circuit 70 is operated to cause sequential entry of the two aberrant signal complexes. The first aberrant signal complex is found in hold register 74 is initially transferred to entry register 72 and thereafter second aberrant signal complex, as from aberrant signal complex input register 60 or classifier 62, is transferred to the entry register so that the two sequential aberrant signal complexes appear in sequence in electrocardiogram 44. In the event a third sequential aberrant signal complex appears, it will be supplied to entry register 72 in the same manner as the second aberrant signal complex.

Various modes of carrying out the invention are contemplated as being within the scope of the following claims particularly pointing out and distinctly claiming the subject matter which is regarded as the invention.

I claim:

1. A method of producing an electrocardiogram on a paper record movable at a slow speed and a fast speed, said electrocardiogram containing the typical and aberrant ekg signal complexes found in the electrocardiographic heart beat data from the patient, said method reducing the quantity of data so recorded by the elimination of redundancies and comprising:

identifying, in the electrocardiographic patient data, the ekg signal complexes associated with each heart beat;

establishing an ekg signal complex pattern from the complexes so identified exemplifying the typical ekg signal complexes in the patient data;

recording the ekg signal complex pattern on the movable record at the slow speed;

detecting ekg signal complexes in the patient data which are aberrant;

recording the aberrant ekg signal complex on the movable record at the fast speed.

2. The method of claim 1 further including the step of establishing a coordinating relationship between the pattern and the aberrant signal complex and the recording of the aberrant ekg signal complex is further defined as recording the aberrant ekg signal complex on the movable record responsive to the coordinating relationship at the fast speed.

3. The method of claim 2 wherein the step of establishing the coordinating relationship further comprises defining a predetermined relationship between the aberrant complex and the last typical complex in the patient data and establishing the same relationship between the ekg signal complex pattern and the aberrant signal complex.

4. The method of claim 3 wherein the step of establishing the coordinating relationship further comprises defining a predetermined point in the last typical complex in the patient data and establishing the corresponding point in the ekg signal complex pattern as a switch-over point for recording the aberrant ekg signal complex.

5. The method of claim 4 wherein the step of recording the aberrant signal complex on the movable record is further defined as accelerating the record to the fast speed when the aberrant complex is detected; completing the recording of the ekg signal complex pattern at the fast speed; and switching over to the recording the aberrant ekg signal complex at the fast speed at the switch over point.

6. The method of claim 3 wherein the step of establishing the coordinating relationship further comprises establishing corresponding reference points in the aberrant signal complex, the last typical complex, and the ekg signal complex pattern, defining by means of the reference points in the aberrant signal complex and last typical complex a predetermined point and establishing the corresponding point in the ekg signal complex pattern by means of the reference point in the pattern.

7. The method according to claim 6 wherein the step of establishing the coordinating relationship further comprises defining the predetermined point and establishing the corresponding point to include a portion of the last typical beat of the ekg data.

8. The method according to claim 2 wherein the aberrant signal complexes occur repetitiously in the patient data and wherein said method further includes the step of ascertaining the proportion of aberrant signal complexes to typical signal complexes appearing in patient data and the recording steps are further defined as recording a corresponding number of ekg signal complex patterns and aberrant signal complexes in the electrocardiogram.

9. The method according to claim 8 wherein said method further comprises selecting an aberrant signal complex from said patient data suitable for recording and recording same in the electrocardiogram.

10. The method of claim 9 wherein said method further comprises determining, by means of said proportion, the number of aberrant signal complexes which will appear in the patient data during the recording of the ekg signal complex patterns; sensing receipt of a corresponding number (N) of aberrant signal complexes; and recording the Nth aberrant signal complex.

11. The method of claim 10 wherein the determining step is further defined as reducing the determined number of aberrant signal complexes by a number selected in accordance with the coordinating relationship of the ekg signal complex pattern and the aberrant signal complex and sufficient to maintain the correct proportion of ekg signal complex patterns and aberrant signal complexes in the electrocardiogram.

12. The method of claim 11 wherein the determining step is further defined as reducing the determined number of aberrant signal complexes by a number equal to the number of aberrant signal complexes corresponding to a preselected portion of an ekg signal complex pattern.

13. The method of claim 12 wherein the determining step is further defined as reducing the determined number of aberrant signal complexes by a number corresponding to half an ekg signal complex pattern.

14. The method of claim 8 further defined as including the step of recording the initial occurrence of an aberrant signal complex in the electrocardiogram.

15. The method of claim 8 further defined as including the step of recording the sequential occurrence of aberrant signal complexes in the electrocardiogram.

16. The method of claim 8 wherein said method further comprises selecting an aberrant signal complex of each type from said patient data suitable for recording and recording same in the electrocardiogram.

17. The method of claim 16 wherein said method further comprises ascertaining the proportion of the total number of aberrant signal complexes of all types to typical signal complexes appearing in the patient data; determining by means of said proportion, the total number of aberrant signal complexes which will appear in the patient data during the recording of the ekg signal complex patterns; sensing the receipt of a corresponding number (N) of aberrant signal complexes of each type; and recording the Nth aberrant signal complex of each type.

18. The method of claim 17 wherein the determining step is further defined as reducing the determined number of aberrant signal complexes by a number selected in accordance with the coordinating relationship of the ekg signal complex pattern and the aberrant signal complex and sufficient to maintain the correct proportion of ekg signal complex patterns and aberrant signal complexes.

19. The method according to claim 18 wherein the determining step is further defined as reducing the determined number of aberrant signal complexes by a number equal to the number of aberrant signals corresponding to a preselected portion of an ekg signal complex.

20. The method according to claim 19 wherein the determining step is further defined as reducing the determined number of aberrant signal complexes by a number corresponding to half an ekg signal complex pattern.

21. The method of claim 2 wherein aberrant signal complexes of differing types occur repetitiously in the patient data and wherein said method further includes the step of classifying the aberrant signal complexes as to type; ascertaining the proportion of differing types aberrant signal complexes to typical signal complexes appearing in patient data and the recording steps are further defined as recording a corresponding number of ekg signal complex patterns and aberrant signal complex of differing types in the electrocardiogram.

22. The method of claim 21 wherein the step of classifying the aberrant signal complexes is further defined as storing the initial occurrence of differing types of aberrant signal complexes and comparing subsequently received aberrant signal complexes with the stored data to classify and subsequently received aberrant signal complexes as to type.

23. The method of claim 22 wherein the comparison step is further defined as comparing subsequently received aberrant signal complexes on the basis of shape and timing for classifying the subsequently received aberrant signal complexes as to type.

24. The method of claim 23 wherein the comparison step is further defined as comparing the subsequently received aberrant signal complexes against the ekg signal complex pattern for classifying as to type with respect to timing.

25. The method according to claim 22 further defined as including the step of recording the initial occurrence of an aberrant signal complex of each type in the electrocardiogram.

26. The method according to claim 22 further defined as including the step of recording the sequential occurrence of aberrant signal complexes in the electrocardiogram.

27. The method according to claim 22 further defined as including the step of recording each occurrence of preselected types of aberrant signal complexes.

28. The method of claim 1 wherein the step of identifying the ekg signal complexes in the patient data includes sensing a preselected magnitudinal characteristic in each heart beat of the ekg data.

29. The method of claim 28 wherein the identifying step further includes selecting in the patient data a sufficient portion thereof adjacent said magnitudinal characteristic to comprise the complex associated with a heart beat.

30. The method of claim 29 wherein the identifying step is further defined as ascertaining the interval between heart beats in the patient data and selecting the portion of the patient data surrounding each magnitudinal characteristic corresponding to one such interval to comprise a signal complex.

31. The method of claim 1 wherein the incoming data is in analog form, said method including the preliminary step of converting the data to digital form and the recording steps are defined as converting the digital data to an analog recording.

32. The method of claim 1 wherein the step of establishing an ekg signal complex pattern is further defined as forming an ekg signal complex pattern, comparing the pattern so established with subsequent ekg signal complexes to ascertain any differences therebetween and altering the established ekg signal complex pattern responsive to differences within predetermined amounts to reform the ekg signal complex pattern.

33. The method according to claim 32 wherein the step of establishing the ekg signal complex pattern is further defined as altering the established ekg signal complex pattern by a predetermined portion of any differences to reform the ekg signal complex pattern.

34. The method of claim 1 wherein the step of detecting aberrant signal complexes is further defined as detecting ekg signal complexes in the patient data which are aberrant with respect to the ekg signal complex pattern.

35. The method according to claim 34 wherein the step of detecting aberrant ekg signal complexes is further defined as detecting complexes as aberrant which differ from the ekg signal complex pattern in excess of a predetermined amount.

36. The method of claim 34 wherein the step of detecting aberrant ekg signal complexes is further defined as ascertaining the heart beat rate reflected in the ekg signal complexes in the patient data; comparing this heart beat rate with that reflected by the ekg signal complex pattern; and identifying a complex as aberrant when the heart beat rate difference exceeds a predetermined amount.

37. The method of claim 34 wherein the step of detecting aberrant ekg signal complexes is further defined as ascertaining the amplitude of the ekg signal complexes in the patient data; comparing the amplitude of the complexes with that of the ekg signal complex pattern; and identifying a complex aberrant when the amplitudinal difference exceeds a predetermined amount.

38. The method of claim 37 wherein the step of detecting aberrant ekg signal complexes is further defined as ascertaining the amplitude of a predetermined sample of the ekg signal complexes in the patient data; comparing the amplitude of the sampled data with a corresponding portion of the ekg signal complex pattern; and identifying a complex as aberrant when the amplitudinal difference exceeds a predetermined amount.

39. The method of claim 38 wherein, in the comparative step, the amplitudinal difference is determined by squaring and summing the amplitudinal differences between the sampled data and the corresponding portion of the ekg signal complex pattern.

40. The method according to claim 37 wherein the step of detecting an aberrant ekg signal complex is further defined as ascertaining the heart beat rate reflected in the ekg signal complexes in the patient data; comparing this heart beat rate with that reflected by the ekg signal complex pattern; and identifying a complex as aberrant when the heart beat rate or amplitudinal difference exceeds a predetermined amount.

41. Apparatus for producing an electrocardiogram containing the typical and aberrant signal complexes found in the electrocardiographic heart beat signal from the patient, said apparatus comprising:
input means for receiving the electrocardiographic signals from the patient;

signal processing means coupled to said input means for identifying the ekg signal complex associated with each heart beat;

comparator means coupled to said signal processing means for ascertaining typical and aberrant signal complexes;

pattern register means coupled to said comparator for establishing a typical ekg signal complex pattern from said typical ekg signal complexes;

recording means operable at a slow speed and at a fast speed for making a graphic recording, said means being coupled to said pattern register for recording said pattern at the slow speed; and aberrant signal complex signal processing means coupled to said comparator means for receiving the aberrant signal complexes, said signal processing means being coupled to said recording means for recording the aberrant signal complexes at the fast speed.

42. The apparatus of claim 41 including coordinating means coupled to said pattern register means and to said aberrant signal complex register means for coordinating the operation of said recording means and the slow speed recording of said pattern and fast speed recording of said aberrant signal complexes.

43. The apparatus of claim 41 including analog-to-digital conversion means couplable to said input means for converting the analog electrocardiographic signals from the patient to digital data and wherein the recording means includes digital-to-analog conversion means for making an analog graphic recording.

44. The apparatus of claim 41 wherein said signal processing means includes means for sensing a preselected characteristic in the electrocardiographic signals from the patient for identifying the ekg signal complexes.

45. The apparatus of claim 44 wherein said signal processing means includes means for defining the portion of electrocardiographic signals comprising the signal complex associated with each heart beat.

46. The apparatus of claim 41 wherein said pattern register means is further coupled to said comparator for providing said pattern to said comparator for comparison against the ekg signal complexes to ascertain typical or aberrant signal complexes.

47. The apparatus of claim 46 wherein said pattern register means includes updating means for altering said established signal complex pattern responsive to differences of a predetermined amount resulting from said comparison.

48. The apparatus of claim 47 wherein said updating means is further defined as means for altering the established signal complex pattern by a predetermined portion of the difference resulting from comparison.

49. The apparatus of claim 46 wherein said comparator includes means for comparing the heart beat rate of the signal complexes with that of the ekg signal complex pattern.

50. The apparatus of claim 46 wherein said comparator includes means for comparing the magnitude of the signal complexes with that of the ekg signal complex pattern.

51. The apparatus of claim 50 wherein said magnitude comparison means includes means for selecting a predetermined sample of each ekg signal complex and a corresponding sample of said pattern and comparing the magnitudinal differences of the samples.

52. The apparatus of claim 51 wherein said magnitude comparison means includes means for squaring and summing the magnitudinal differences and for comparing the sum to a predetermined level for ascertaining aberrancy.

53. The apparatus of claim 41 further defined as for use with electrocardiographic heart beat signals in which aberrant signal complexes occur repetitiously, said aberrant signal complex signal processing means including counting means coupled to said comparator for ascertaining the proportion of aberrant to typical signal complexes appearing in the heart beat signals, said counting means being coupled to said recording means for recording a corresponding number of ekg signal complex patterns and aberrant signal complexes in the electrocardiogram.

54. The apparatus of claim 53 wherein said counting means is further defined as means for selecting a given aberrant signal complex from the aberrant signal complexes in the electrocardiographic signals from the patient suitable for recording and recording same.

55. The apparatus of claim 54 wherein said counting means is further defined as establishing a number in accordance with the proportion of aberrant to typical signal complexes and counting said aberrant signal complexes for selecting the given aberrant signal complex in accordance with the established number.

56. The apparatus of claim 55 wherein said counting means is further defined as containing means for altering the number in the counter by an amount sufficient to secure proper entry of the aberrant signal complexes in the electrocardiogram.

57. The apparatus of claim 55 suitable for use with electrocardiographic heart beat signals in which aberrant signal complexes of differing types occur repetitiously and wherein said aberrant signal complex signal processing means includes classifier means coupled to said comparator and said counter for classifying the aberrant signal complexes as to type and wherein said counter counts said types of aberrant signal complexes for selecting aberrant signal complexes for recording in the electrocardiogram.

58. The apparatus of claim 57 wherein said classifier means includes aberrant signal complex storage means for storing aberrant signal complex data for comparative purposes.

59. The apparatus of claim 53 wherein said aberrant signal complex signal processing means includes means coupled to said comparator and to said recording means for recording the initial occurrences of an aberrant signal complex in the electrocardiogram.

60. The apparatus of claim 59 wherein said classifier means is coupled to said ekg signal complex pattern register means for receiving said pattern for comparative purposes.

61. The apparatus of claim 53 wherein said aberrant signal complex signal processing means includes means coupled to said comparator and to said recording means for recording sequential occurrences of aberrant signal complexes in the electrocardiogram.

* * * * *